United States Patent [19]

Nakagawa et al.

[11] Patent Number: 5,409,546
[45] Date of Patent: Apr. 25, 1995

[54] METHOD FOR CLEANING, PRESERVING AND DISINFECTING CONTACT LENSES

[75] Inventors: Akira Nakagawa; Yoshiko Oi, both of Nagoya, Japan

[73] Assignee: Tomei Sangyo Kabushiki Kaisha, Nagoya, Japan

[21] Appl. No.: 133,329

[22] Filed: Oct. 8, 1993

[30] Foreign Application Priority Data

Oct. 8, 1992 [JP] Japan ................... 4-296299

[51] Int. Cl.6 .......................... B08B 3/08; B08B 3/10; B08B 7/00
[52] U.S. Cl. ...................................... 134/42
[58] Field of Search .......................... 134/42

[56] References Cited

U.S. PATENT DOCUMENTS

| 4,614,549 | 9/1986 | Ogunbiyi et al. | 134/42 |
| 5,281,277 | 1/1994 | Nakagawa et al. | 134/42 |
| 5,314,823 | 5/1994 | Nakagawa | 435/264 |

FOREIGN PATENT DOCUMENTS

| 0141607 | 5/1985 | European Pat. Off. |
| 0462460 | 12/1991 | European Pat. Off. |
| 0508381 | 10/1992 | European Pat. Off. |
| WO85/03247 | 8/1985 | WIPO |

OTHER PUBLICATIONS

Database WPI, Derwent Publications Ltd., AN 92-337367, JP-A-4 243 215, Aug. 31, 1992.

*Primary Examiner*—Michael Lewis
*Assistant Examiner*—Zeinab El-Arini
*Attorney, Agent, or Firm*—Oblon, Spivak, McClelland, Maier & Neustadt

[57] ABSTRACT

A method for cleaning and preserving a contact lens, characterized by using a treating solution containing an effective amount of a serine protease derived from bacteria belonging to genus Bacillus, a metal chelating agent, and boric acid and/or borax which stabilizes the serine protease at room temperature and having the osmotic pressure adjusted to a level of from 200 to 600 mOsm/kg-water, which method comprises dispensing the treating solution at the time of treatment, and immersing a contact lens in the dispensed treating solution.

19 Claims, No Drawings

METHOD FOR CLEANING, PRESERVING AND DISINFECTING CONTACT LENSES

The present invention relates to a method for cleaning, preserving and disinfecting contact lenses. Particularly, it relates to a treating method whereby contact lenses can be cleaned, preserved or disinfected simply by using only a single treating solution, irrespective of whether they are hydrophilic or hydrophobic contact lenses.

BACKGROUND OF THE INVENTION

Contact lenses are generally classified into hydrophilic contact lenses and hydrophobic contact lenses. Irrespective of the types of contact lenses, soils such as proteins, lipids or inorganic substances derived from tear or sebum will deposit on such contact lenses, and it is necessary to clean them periodically. Especially, in the case of hydrophilic contact lenses, bacteria or fungi are likely to deposit thereon, and it is also necessary to disinfect them by a method such as thermal or chemical disinfection.

To remove protein soils deposited on a contact lens, it has been common to clean the contact lens with a cleaning agent containing a protease. However, proteases are instable in an aqueous solution. For example, a commercially available serine protease derived from bacteria of genus Bacillus (Subtilisin A, manufactured by Novo Nordisk Bioindustry Japan K.K.) loses its enzymatic activity by about 70%, when it is kept in an aqueous solution at pH 7 at 25° C. for 24 hours. Therefore, when a cleaning agent containing a protease is to be provided in a liquid form, it is necessary to incorporate an enzyme stabilizer to maintain the enzymatic activity for a long period of time.

For example, Japanese Unexamined Patent Publications No. 180515/1989 and No. 168224/1990 propose to incorporate a water-miscible organic liquid in a proportion of at least 50% by weight for stabilization of an enzyme. Further, Japanese Unexamined Patent Publications No. 93919/1992 and No. 143718/1992 propose to incorporate a polyhydric alcohol in a proportion of at least 20% by weight. Still further, Japanese Unexamined Patent Publication No. 161920/1992 proposes a cleaning agent containing a saccharide as an enzyme stabilizer.

However, each of these cleaning agents contains an enzyme stabilizer at a high concentration, so that its osmotic pressure exceeds a physiological level, whereby there will be a problem of deforming contact lenses or irritating eyes, when it is applied to hydrophilic contact lenses as it is. Accordingly, when such a cleaning agent is used for cleaning or preserving hydrophilic contact lenses, it is necessary to dilute it with a large amount of purified water or a preserving solution having a low osmotic pressure, to lower the osmotic pressure to a physiological level.

However, such a method wherein a protease-containing cleaning agent must be diluted every time for each cleaning treatment of contact lenses, not only requires a cumbersome diluting operation, but also has a problem that if the cleaning agent is not diluted homogeneously, a deformation is likely to result in the contact lenses thereby treated, or that if the cleaning agent is not diluted to a proper concentration, the osmotic pressure will be improper, which brings about irritation to eyes. Further, if such a cleaning agent is diluted to a physiological osmotic pressure level, the enzyme stability will deteriorate extremely in a short period of time, and the cleaning effect will thereby be lowered, whereby it is impossible to clean hydrophilic contact lenses during their preservation.

Further, Japanese Unexamined Patent Publication No. 121416/1985 proposes a method wherein a contact lens is heated in an aqueous solution containing a protease to simultaneously clean and disinfect it. However, the method also has a problem that the protease is easily inactivated in an aqueous solution, and stabilization of the protease is desired.

Though boric acid and borax are often used in an enzyme-containing cleaning agent as buffer agents (Japanese Unexamined Patent Publication No. 121417/1985), they are also known to have an enzyme stabilizing effect, when used in combination with a polyhydric alcohol (Japanese Unexamined Patent Publications No. 51015/1992 and No. 143718/1992). However, this combination cannot practically be applied to a cleaning agent for hydrophilic contact lenses, because the osmotic pressure will thereby be above the physiological level.

On the other hand, an attempt has been made to improve the cleaning effect of an enzyme-containing cleaning agent. On the basis that inorganic salts, such as calcium salts, in tear are likely to form complexes with proteins, which deposit on surface of contact lenses, it is known to incorporate a metal chelating agent to such a cleaning agent to remove such soils and thereby to improve the protein-removing effect by the enzyme.

However, a metal chelating agent is known to lower the stability of a serine protease extremely. Therefore, it has been common to add a metal chelating agent, not to a protease-containing cleaning agent, but to a diluting solution for such a cleaning agent, so that the metal chelating agent is separated from the enzyme until the cleaning agent is used for treatment. Therefore, users have been obliged to have both an enzyme-containing cleaning agent and a diluting solution.

Further, it has been proposed to incorporate a metal chelating agent and a protease into the same solution, by using a certain specific metal chelating agent to minimize the adverse effect to the enzyme stability (Japanese Unexamined Patent Publication No. 51015/1992). However, this method has a disadvantage that the metal chelating effect is thereby weak, so that the cleaning power will be low.

SUMMARY OF THE INVENTION

The present invention has been made under these circumstances, and it is an object of the present invention to facilitate such treatment as cleaning, preserving or disinfecting contact lenses with respect to both hydrophobic and hydrophilic contact lenses, by using only a single liquid cleaning agent with excellent cleaning effect, wherein a protease is stabilized at a physiological osmotic pressure.

As a result of an extensive research to accomplish the above object, the present inventors have found that a serine protease derived from bacteria of genus Bacillus can be stabilized by boric acid or borax in the presence of a metal chelating agent, whereby the enzymatic activity can be maintained for a long period of time at a physiological osmotic pressure level, and the cleaning effect can also be improved. The present invention has been accomplished on the basis of this discovery.

Thus, the present invention provides a method for cleaning and preserving a contact lens, characterized by using a treating solution containing an effective amount of a serine protease derived from bacteria belonging to genus Bacillus, a metal chelating agent, and boric acid and/or borax which stabilizes the serine protease at room temperature and having the osmotic pressure adjusted to a level of from 200 to 600 mOsm/kg-water, which method comprises dispensing the treating solution at the time of treatment, and immersing a contact lens in the dispensed treating solution.

The present invention also provides a method for cleaning and disinfecting a contact lens, characterized by using a treating solution containing an effective amount of a serine protease derived from bacteria belonging to genus Bacillus, a metal chelating agent, and boric acid and/or borax which stabilizes the serine protease at room temperature, and having the osmotic pressure adjusted to a level of from 200 to 600 mOsm/kg-water, which method comprises dispensing the treating solution at the time of treatment, immersing a contact lens in the dispensed treating solution to clean it, followed by heating the treating solution to a temperature of from 80° to 100° C. to disinfect the contact lens.

Further, in the present invention, the treating solution preferably contains from 0.5 to 2% (w/v) of a polyhydric alcohol and/or from 0,001 to 1% (w/v) of a nonionic surfactant.

In the present invention, the immersion for cleaning treatment of contact lenses is conducted advantageously at a temperature of from room temperature to 58° C.

In short, in the treating solution used in the present invention, the protease is effectively stabilized at a physiological osmotic pressure even in the presence of the metal chelating agent, and one-pack system of the protease and the metal chelating agent is advantageously accomplished. Therefore, even after a long period of storage, the treating solution has an excellent cleaning effect, owing to the protease and the metal chelating agent. Further, since the osmotic pressure is adjusted to a physiological level from the beginning, the treating solution requires no diluting operation and can be applied by itself to all kinds of contact lenses irrespective of whether they are hydrophobic or hydrophilic, simply by dispensing a necessary amount of the treating solution at the time of treatment. The treating solution is characterized in that it is free from a problem of deforming contact lenses or irritating eyes.

Simply by immersing contact lenses in the dispensed treating solution, cleaning and preserving of contact lenses can be accomplished not only easily and safely but also with excellent cleaning effect. By immersing contact lenses in the dispensed treating solution and heating the treating solution, cleaning and disinfection of contact lenses can be accomplished very simply. Namely, according to the present invention, treatment of contact lenses such as cleaning, preservation or disinfection can be accomplished very simply by using only a single treating solution i.e. simply by dispensing it for use at the time of treatment.

In the present invention, the enzyme stabilizing effect of the treating solution may further be improved by an addition of a certain amount of a polyhydric alcohol to the treating solution, and the cleaning effect of the treating solution may further be improved by an addition of a certain amount of a nonionic surfactant to the treating solution. By conducting the immersion for cleaning treatment at a temperature of from room temperature to 58° C., a strong cleaning power can be obtained while the inactivation of the enzyme is effectively suppressed.

Proteases are generally classified into serine proteases, thiol proteases, carboxyl proteases and metal proteases, depending upon their active sites. They are also classified into three of microorganism-, plant- and animal-derived proteases, depending upon their origins. Microorganism-derived proteases are further classified into bacteria-, actinomycete-, mold- and yeast-derived proteases. Among those proteases thus classified, only serine proteases produced by bacteria belonging to genus Bacillus can be used and incorporated as an essential component in the treating solution to be used in the present invention.

Recently, various serine proteases modified by genetic engineering have been commercially available, and such serine proteases may also be used for the present invention. Specifically, Esperase, Subtilisin A, Savinase, Durazyme (manufactured by Novo Nordisk Bioindustry Japan K.K.), Protease N "Amano", Protease S "Amano" (manufactured by Amano Pharmaceutical K.K.) and Bioprase (manufactured by Nagase Seikagaku Kogyo K.K.) may be mentioned. The protease content is usually in a range of from 0.0001 to 1% (w/v), preferably in a range of from 0.01 to 0.5% (w/v) to obtain an effective cleaning power, although such a content can not generally be defined since each protease has its own specific activity.

The metal chelating agent contained as another essential component in the treating solution used in the present invention, is known to reduce the stability of the serine protease, while it removes soils of inorganic salts such as calcium salts, which form complexes with proteins and thus improve the protein-removing effect. According to the present invention, it has been made possible to secure the enzyme stability even in the presence of a metal chelating agent, by the combination of such a metal chelating agent, the aforementioned serine protease derived from bacteria belonging to genus Bacillus and boric acid and/or borax, which will be described hereinafter.

Specific examples of the metal chelating agent include ethylenediamine tetraacetic acid, nitrilotriacetic acid and their salts. The content of the metal chelating agent is usually from 0.01 to 1% (w/v). If such a metal chelating agent is not contained, the cleaning effect will be reduced, although the enzyme stability may be further improved.

The treating solution used in the present invention also contains boric acid and/or borax as an essential component, which serves as an enzyme stabilizer. Though its enzyme stabilizing mechanism is unknown, if its concentration is too low, no enzyme stabilizing effect will be obtained, and if its concentration is too high, irritation to eyes is likely to result, or the cleaning effect is likely to be reduced. Accordingly, boric acid and/or borax is incorporated usually at a concentration of from 0.05 to 2% (w/v), preferably from 0.2 to 1% (w/v).

A polyhydric alcohol may be added to the treating solution to improve the enzyme stabilizing effect. If the concentration of the polyhydric alcohol is too low, the enzyme stabilizing effect can not be obtained. On the other hand, if the concentration is too high, the cleaning effect will be reduced. Accordingly, the amount of the polyhydric alcohol to be added is usually in the range of from 0.5 to 2% (w/v). Specifically glycerol, diethylene glycol, polyethylene glycol or sorbitol may, for example, be used.

In the present invention, the osmotic pressure of the treating solution is required to be adjusted to a physiological osmotic pressure, i.e. to a level of from 200 to 600 mOsm/kg-water. If the osmotic pressure is below this range, the enzyme stability tends to be poor, and if the osmotic pressure is above this range, hydrophilic contact lenses are likely to be deformed, and irritation to eyes will result. Therefore, a tonicity-controlling agent may be added to adjust the osmotic pressure within the above range, as the case requires. There is no particular restriction to the tonicity-controlling agent to be used, and various buffering agents which will be described hereinafter and tonicity-controlling agents such as sodium chloride, potassium chloride and glycerol, may be used, as the case requires.

The pH of the treating solution is preferably within a range of from 6 to 8. If the pH is higher than 8, irritation to eyes is likely to result, and if the pH is lower than 6, the enzymatic activity of the serine protease derived from bacteria belonging to genus Bacillus is likely to be reduced. Therefore, a buffering agent may be added to adjust the pH of the treating solution within this range, as the case requires. Boric acid or a salt of boric acid, an organic acid such as citric acid or acetic acid, or a salt such as a sodium or potassium salt thereof, or an amino acid such as glycine, may, for example, be used.

Further, a surfactant may preferably be added to the treating solution to remove lipid soils derived from sebum, etc. As such a surfactant, the one which is highly safe to a vital body and presents no adverse effect to contact lenses, is desirable. In this respect, a nonionic surfactant is suitable. Specific examples of such a surfactant include polyoxyethylene-polyoxypropylene-block polymers, condensates of ethylenediamine with polyoxyethylene-polyoxypropylene, glycerol fatty acid esters, polyoxyethylene glycerol fatty acid esters, sucrose alkyl esters, polyethylenealkylamines, polyoxyethylene sorbitane fatty acid esters and polyoxyethylene hardened castor oil. Among them, polyoxyethylene sorbitol fatty acid esters are preferred.

Especially, tetra-fatty acid polyoxyethylene sorbitols of the following structural formula:

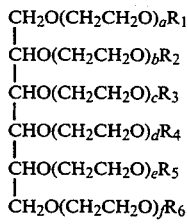

wherein four among $R_1$ to $R_6$ are $C_{12-18}$ saturated or unsaturated fatty acid residues (RCO—wherein R is a saturated or unsaturated fatty acid group) and the remaining two among $R_1$ to $R_6$ are hydrogen atoms, have such characteristics that they are highly safe and have a high cleaning effect. Among such sorbitols, those with an average number of mols of added polyethylene (a+b+c+d+e+f) of from 20 to 50 are advantageously selected, because of their excellent characteristics such that they have high solubilities and they are scarcely adsorbed on contact lenses.

If the amount of the surfactant is too small, the cleaning power will be insufficient. On the other hand, if it is too much, no further increase in the cleaning power can be expected. Accordingly, such a surfactant is added usually in an amount of from 0.001 to 1% by weight.

Preservatives may also be added to the treating solution to prevent propagation of fungi during the storage, as the case requires. For example, sorbic acid, benzoic acid, biguanides or salts thereof and quaternary ammonium salts may optionally be employed.

In the treating solution thus prepared, the protease maintains its activity at room temperature for a long period of time, even at a physiological osmotic pressure in the presence of a metal chelating agent. Specifically, it is possible to attain a remaining enzymatic activity of more than 60%, or more than 70% with a preferred formulation, after two months at 25° C. Accordingly, such a treating solution can be stored for a long period of time, while it can be applied by itself to both hydrophobic and hydrophilic contact lenses without dilution by dispensing it at the time of treatment. With such a treating solution, no dilution is required, unlike a conventional enzyme-containing treating solution. Accordingly, the treating operation is simple and not cumbersome, and there is no problem of deforming contact lenses and irritating eyes. If the remaining enzymatic activity is substantially lower than 50%, the cleaning effect will be low, and it will be difficult to use such a treating solution practically.

Using such a treating solution, contact lenses may be cleaned simply by immersing them in the dispensed treating solution. The temperature for the immersion is selected within a range of from room temperature to 58° C., preferably from about 40° C. to about 55° C., more preferably from about 45° C. to about 50° C. If the temperature is too low, the cleaning effect will be insufficient. On the other hand, if it is too high, the protease loses its activity, whereby no adequate cleaning effect will be obtained. The time for the immersion is usually at least 15 minutes, preferably from about 30 minutes to about 3 hours, more preferably from about 1 hour to about 2 hours. However, since the treating solution can be used also as a preserving solution, a contact lens can be cleaned while being preserved. The period of immersion for preservation is not especially restricted. Further, to improve the cleaning effect, the contact lens may be rubbed for cleaning on a palm or a puff before or after the immersion, if necessary.

In the case of hydrophilic contact lenses, disinfecting treatment is required in addition to cleaning treatment. Therefore, a method is advantageously selected, which comprises immersing contact lenses in the dispensed treating solution and heating the treating solution to a temperature of from 80° to 100° C., preferably about 100° C. Thus, cleaning and thermal disinfection can be conducted successively, and the treatment of hydrophilic lenses can be accomplished very simply. The disinfection can be conducted by heating for a sufficient period for disinfection, usually from 5 to 30 minutes, preferably from 10 minutes to 20 minutes. For such heating treatment, a heater may be used wherein the temperature is controlled by a microcomputer or the like to a predetermined level. After the disinfection, the contact lens may be stored in the treating solution, or may be taken out from the treating solution and put on the eye, in the same manner as usual.

Now, the present invention will be described in further detail with reference to some Examples for the method for cleaning, preserving and disinfecting a contact lens according to the present invention. However, it should be understood that the present invention is by no means restricted by such specific Examples. Further, it should be understood that in addition to the following Examples and the specific embodiments as described above, various changes, modifications or improvements may be made on the basis of the common knowledge of those skilled in the art without departing from the spirit of the present invention.

EXAMPLES 1 to 5

First, the respective components were weighed as identified in the following Table 1, and dissolved in purified water so that the total volume would be 100 ml, to obtain five types of treating solutions. Then, the pH and the osmotic pressure of each treating solution were measured by a pH-osmometer HOSM-1-Model (manufactured by TOA Electronics Ltd.). The enzymatic activity of each treating solution was measured as described hereinafter. Further, after the storage for 70 days at 25° C., the enzymatic activity of each treating solution was measured again, and the remaining enzymatic activity was calculated. The results are shown in Table 1.

Measurement of the enzymatic activity:

1 ml of a treating solution was added to 5 ml of a 0.6% casein solution (pH 7.0, a 0.05M disodium monohydrogenphosphate aqueous solution) preheated to 37° C., and the mixture was incubated at 37° C. for 10 minutes. Then, 5 ml of a precipitating reagent (a mixed solution comprising 0.11M trichloroacetic acid, 0.22M sodium acetate and acetic acid) was added thereto to terminate the enzymatic reaction, followed by further incubation at 37° C. for 30 minutes. The resulting solution was filtered, and to 1 ml of the filtrate, 2.5 ml of 0.55M sodium carbonate and 0.5 ml of Folin reagent were added. After incubating this solution at 37° C. for 30 minutes, absorption A at 660 nm was measured. Separately, 5 ml of the above precipitating reagent and 5 ml of the casein solution were added to 1 ml of a treating solution, followed by incubation at 37° C. for 30 minutes. The resulting solution was filtered, and to 1 ml of the filtrate, 2.5 ml of 0.55M sodium carbonate and 0.5 ml of Folin reagent were added. After incubation at 37° C. for 30 minutes, absorption Ao at 660 nm was measured. The enzymatic activity capable of forming nonprotein substances showing an absorption at 660 nm in an amount corresponding to $1\times10^{-6}$ g of tyrosine per minute, was defined as 1 unit.

Enzymatic activity (units/ml)=$[(A-Ao)/As]\times 50\times(11/10)$ wherein As=absorption by 50 g/ml of tyrosine at 660

Remaining enzymatic activity (%)=(Enzymatic activity after storage/Initial enzymatic activity) $\times 100$

TABLE 1

| | | | | | (g/100 ml) |
| Components | Treating solution | | | | |
| | Example 1 | Example 2 | Example 3 | Example 4 | Example 5 |
| --- | --- | --- | --- | --- | --- |
| Subtilisin A *1 | 0.05 | 0.085 | — | — | 0.05 |
| Esperase 8.0 L *2 | — | — | 0.2 | — | — |
| Savinase *3 | — | — | — | 0.1 | — |
| Boric acid | 0.38 | 0.37 | — | 1.00 | 0.36 |
| Borax | 0.09 | 0.07 | 0.45 | 0.51 | 0.04 |
| Citic acid monohydrate | — | — | 0.16 | — | — |
| Glycerol | 1.43 | 1.46 | — | — | — |
| polyethylene glycol 400 | — | — | 2.0 | — | — |
| Sorbitol | — | — | — | 0.8 | — |
| NaCl | — | — | 0.35 | — | 0.67 |
| Disodium ethylenediamine-tetraacetate dihydrate | 0.05 | 0.05 | 0.05 | — | 0.05 |
| Sodium nitrilotriacetate monohydrate | — | — | — | 0.1 | — |
| Potassium sorbate | 0.15 | — | 0.15 | — | 0.15 |
| Sodium benzoate | 0.20 | 0.20 | — | 0.20 | — |
| Polyoxyethylene (30) tetraoleate | 0.02 | 0.02 | — | 0.20 | — |
| Osmotic pressure (mOsm/kg) | 303 | 288 | 286 | 291 | 324 |
| pH | 7.15 | 6.80 | 7.50 | 7.01 | 7.10 |
| Enzymatic activity (units/ml) | 94.9 | 164 | 299.7 | 167.3 | 91.4 |
| Remaining enzymatic activity at 25° C. after 70 days (%) | 86 | 76 | 92 | 90 | 83 |

Note *1 to 3: Serine proteases derived from bacteria belonging to Bacillus, manufactured by Novo Nordisk Bioindustry Japan K.K.

COMPARATIVE EXAMPLE 1

A treating solution was prepared by incorporating 1.0% (w/v) of trisodium citrate dihydrate instead of boric acid and borax in the treating solution of Example 1. This treating solution had an osmotic pressure of 334 mOsm/kg, a pH of 7.13 and an initial enzymatic activity of 112 units/ml. This treating solution was stored at 25° C. for 70 days, whereupon the remaining enzymatic activity was examined and found to be 42%.

From the comparison between Example 1 and Comparative Example 1, it is apparent that when boric acid and borax are incorporated, the enzymatic stability increases.

EXAMPLES 6 and 7 and COMPARATIVE EXAMPLE 2

With respect to the treating solution of Example 5, the content of NaCl was changed as indicated in the following Table 2, to obtain treating solutions having various osmotic pressures. Then, each treating solution was stored at 25° C. for 70 days, and the remaining enzymatic activity was measured. The results are also shown in Table 2.

From the comparison between Examples 5 to 7 and Comparative Example 2, it is apparent that when the osmotic pressure of the treating solution is from 200 to 600 mOsm/kg, the enzyme stability increases.

TABLE 2

|  | Example 6 | Example 7 | Comparative Example 2 |
|---|---|---|---|
| NaCl (%, w/v) | 0.3 | 1.50 | 0.1 |
| Osmotic pressure (mOsm/kg) | 203 | 582 | 139 |
| Remaining enzymatic activity at 25° C. after 70 days (%) | 82 | 88 | 44 |

COMPARATIVE EXAMPLES 3 to 5

Treating solutions were prepared by changing the enzyme in the treating solution of Example 1 to Papain W-40 (manufactured by Amano Pharmaceutical K.K., a thiol protease derived from plants), Actinase AS (manufactured by Kaken Pharmaceutical Co., Ltd., a serine protease derived from actinomycetes), and Pancreatin F (manufactured by Amano Pharmaceutical K.K., a protease derived from animals), respectively. Then, each treating solution was stored at 25° C. for 70 days, followed by measurement of the remaining enzymatic activity. The results are shown in the following Table 3.

As is apparent from the comparison between Example 1 and Comparative Examples 3 to 5, only the treating solution containing a serine protease derived from bacteria belonging to Bacillus had an excellent remaining enzymatic activity.

TABLE 3

|  | Comparative Example 3 | Comparative Example 4 | Comparative Example 5 |
|---|---|---|---|
| Enzyme | Papain W-40 | Actinase AS | Pancreatin F |
| Remaining enzymatic activity at 25° C. after 70 days (%) | 5.0 | 2.6 | 22.3 |

EXAMPLE 8

0.1% (w/V) Of egg-white lysozyme, 0.28% (w/v) of sodium chloride, 1.15% (w/v) of disodium hydrogenphosphate and 0.23% (w/v) of sodium dihydrogenphosphate monohydrate were dissolved in purified water to obtain an artificial tear. A hydrophilic contact lens (Menicon Soft MA, manufactured by Menicon Co., Ltd.) was put into a vial filled with 5 ml of the artificial tear, followed by heating at 80° C. for 20 minutes. After cooling, the contact lens was rinsed with physiological saline to obtain an artificially soiled lens. The contact lens was inspected by a dark-field microscope, thereby protein-like soil was observed over the entire surface of the lens. Then, the artificially soiled lens was put into a storage case for a contact lens filled with the treating solution of Example 1, and immersed therein at room temperature (25° C.) overnight. After rinsing it with physiological saline, the lens was inspected by a dark-field microscope, whereby it was observed that the soils were removed cleanly.

EXAMPLE 9

The artificially soiled contact lens prepared in Example 8 was put into a storage case, and the case was filled with the treating solution, followed by heating and cleaning at 50° C. for 60 minutes. After repeating this treatment twice, the lens was rinsed with physiological saline and inspected by a dark-field microscope, whereby it was observed that the soil was cleanly removed.

COMPARATIVE EXAMPLE 6

The artificially soiled contact lens prepared in Example 8 was put into a storage case, and the case was filled with the treating solution prepared in Example 2, followed by heating and cleaning at 60° C. for 60 minutes. This heating treatment was repeated twice, whereupon it was observed that the soil or the contact lens was not removed very much and remained over the entire surface of the contact lens.

From the comparison with Example 9, it is apparent that in a method for cleaning a contact lens according to the present invention, a high cleaning effect can be obtained, when the temperature of the treating solution at the time of heating for cleaning does not exceed 58° C., and the cleaning effect will be reduced, when the temperature is higher than 58° C.

EXAMPLE 10

The treating solution of Example 2 was stored at 25° C. for two months, and an artificially soiled contact lens was cleaned and heated in the stored treating solution, in the same manner as in Example 9. This treatment was repeated twice, whereupon it was observed that the soil on the contact lens was cleanly removed.

COMPARATIVE EXAMPLE 7

The treating solution of Comparative Example 1 was stored at 25° C. for two months, and an artificially soiled lens was cleaned and heated in the stored treating solution, in the same manner as in Example 9. This treatment was repeated twice, whereupon it was observed that the soil on the contact lens was hardly removed.

From the comparison between Example 10 and Comparative Example 6, it is apparent that in a method for cleaning a contact lens according to the present invention, the treating solution has a high cleaning effect even after a long period of storage.

EXAMPLE 11

The diameter and the degree of a hydrophilic contact lens (Menicon MA, manufactured by Menicon Co., Ltd.) were measured by a profile projector (manufactured by Nikon K.K.) and a lens meter (manufactured by Nikon K.K.), respectively, whereby the diameter was found to be 13.0 mm and the degree was found to be −3.00 D. the contact lens was put on a human eye. After 6 hours, the lens was taken off from the eye, rinsed with a preserving solution (Clean Bottle Soak, manufactured by Menicon Co., Ltd.), and then put into a storage case.

Then, 1.2 ml of a treating solution prepared in the same manner as in Example 1, was dispensed into the storage case, and the contact lens was immersed and cleaned therein for 30 minutes. The storage case was set in a boil sterilizer (Menicon Riser Mini, manufactured by Menicon Co., Ltd.), and sterilized for disinfection. Then, it was kept as it was overnight. The rest of the treating solution was stored at 25° C., and a series of treatment which comprised putting on, rinsing, immersing for cleaning, boiling and preserving, was repeated once a day everyday from the next day, by dispensing and using the stored treating solution. After 60 days, the contact lens was examined again, and there was no change in the diameter and the degree. Further, the surface of the lens was inspected by a dark-field microscope, whereby it was found to be clean.

What is claimed is:

1. A method for cleaning and preserving a hydrophilic contact lens, characterized by using an undiluted treating solution containing an effective cleaning and preserving amount of a serine protease derived from bacteria belonging to genus Bacillus, a metal chelating agent, and boric acid and/or borax which stabilizes the serine protease at room temperature and having the osmotic pressure adjusted to a level of from 200 to 600 mOsm/kg-water, wherein the treating solution contains from 0.0001 to 1% (w/v) of the serine protease, from 0.01 to 1% (w/v) of the metal chelating agent, and from 0.05 to 2% (w/v) of the boric acid and/or borax, which method comprises dispensing said undiluted treating solution at the time of treatment; and immersing a hydrophilic contact lens in the dispensed treating solution.

2. The method according to claim 1, wherein after immersing the contact lens in the dispensed treating solution, the treating solution is heated to a temperature of from 80° to 100° C. to disinfect the contact lens.

3. The method according to claim 2, wherein the heating is conducted from 5 to 30 minutes.

4. The method according to claim 1, wherein the treating solution further contains from 0.5 to 2% (w/v) of a polyhydric alcohol.

5. The method according to claim 4, wherein the polyhydric alcohol is selected from the group consisting of glycerol, diethylene glycol, polyethylene glycol and sorbitol.

6. The method according to claim 1, wherein the treating solution further contains from 0.001 to 1% (w/v) of a nonionic surfactant.

7. The method according to claim 6, wherein the nonionic surfactant is a fatty acid ester of polyoxyethylene sorbitol.

8. The method according to claim 1, wherein the metal chelating agent is ethylenediamine tetraacetic acid or its salt.

9. The method according to claim 1, wherein the metal chelating agent is nitrilotriacetic acid or its salt.

10. The method according to claim 1, wherein the serine protease derived from bacteria belonging to genus Bacillus is in an amount of from 0.01 to 0.5% (w/v).

11. The method according to claim 1, wherein the serine protease is stabilized so that more than 60% of the enzymatic activity will remain after two months at 25° C.

12. The method according to claim 1, wherein the serine protease is stabilized so that more than 70% of the enzymatic activity will remain after two months at 25° C.

13. The method according to claim 1, wherein the treating solution has a pH in a range of from 6 to 8.

14. The method according to claim 1, wherein the immersion is conducted at a temperature of from room temperature to 58° C.

15. The method according to claim 1, wherein the immersion is conducted for at least 15 minutes.

16. A method for cleaning and disinfecting a hydrophilic contact lens, characterized by using an undiluted treating solution containing an effective cleaning and disinfecting amount within the range of from 0.0001 to 1% (w/v) of a serine protease derived from bacteria belonging to genus Bacillus, from 0.01 to 1% (w/v) of a metal chelating agent, and from 0.05 to 2% (w/v) of the boric acid and/or borax, which stabilizes the serine protease at room temperature and having the osmotic pressure adjusted to a level of from 200 to 600 mOsm/kg-water, which method comprises dispensing said undiluted treating solution at the time of treatment; immersing a hydrophilic contact lens in the undiluted dispensed treating solution to clean it, followed by heating the treating solution to a temperature of from 80° to 100° C. to disinfect the hydrophilic contact lens.

17. The method according to claim 16, wherein the treating solution further contains from 0.5 to 2% (w/v) of a polyhydric alcohol.

18. The method according to claim 16, wherein the treating solution further contains from 0,001 to 1% (w/v) of a nonionic surfactant.

19. The method according to claim 16, wherein the metal chelating agent is ethylenediamine tetraacetic acid or its salt, or nitrilotriacetic acid or its salt.

* * * * *